United States Patent [19]
Galland et al.

[11] Patent Number: 5,426,254
[45] Date of Patent: Jun. 20, 1995

[54] PROCESS FOR THE SEPARATION OF HYDROGEN FLUORIDE FROM ITS MIXTURES WITH 1,1,1-TRIFLUORO-2-CHLOROETHANE

[75] Inventors: Jean-Michel Galland, Vernaison; René Perdriau; Dominique Rouzies, both of Lyons, all of France

[73] Assignee: d'Elf Atochem S.A., Puteaux, France

[21] Appl. No.: 118,846

[22] Filed: Sep. 10, 1993

[30] Foreign Application Priority Data

Sep. 10, 1992 [FR] France ............... 92 10811

[51] Int. Cl.$^6$ .............................. C07C 17/38
[52] U.S. Cl. .................... 570/180; 570/178; 423/483
[58] Field of Search .................. 570/180, 178

[56] References Cited
U.S. PATENT DOCUMENTS 4,209,470 6/1980 Lorquet ................... 570/180

Primary Examiner—Alan Siegel
Attorney, Agent, or Firm—Morgan & Finnegan

[57] ABSTRACT

The invention relates to the separation of hydrogen fluoride (HF) from its mixtures with 1,1,1-trifluoro-2-chloroethane (F133a).

By settling of the mixture of HF and F133a in the presence of trichloroethylene at a temperature below 0° C., a lower organic phase which is poor in HF and an upper phase which is rich in HF are obtained. The latter can be directly recycled to the fluorination reactor or subjected to a distillation in order to separate, at the head, the HF/F133a azeotrope which is returned to the settler, and to recover, at the foot, practically pure HF. By distillation of the lower phase, the HF/F133a azeotrope which is returned to the settler is separated at the head and a mixture of F133a and trichloroethylene is recovered at the foot. The latter mixture is subjected to a distillation which makes it possible to separate, at the head, pure F133a from trichloroethylene at the foot.

10 Claims, 1 Drawing Sheet

PROCESS FOR THE SEPARATION OF HYDROGEN FLUORIDE FROM ITS MIXTURES WITH 1,1,1-TRIFLUORO-2-CHLOROETHANE

FIELD OF THE INVENTION

The invention relates to the separation of hydrogen fluoride (HF) from its mixtures with 1,1,1-trifluoro-2-chloroethane (F133a) which is a significant synthesis intermediate and can be used especially for the manufacture of 1,1,1,2-tetrafluoroethane (F134a).

The process according to the invention applies more particularly to the separation of unconverted HF contained in the mixtures arising from the manufacture of F133a by fluorination of trichloroethylene or of symmetrical or asymmetrical tetrachloroethane. For reasons of economy, it is necessary to recover HF in the anhydrous form in order to be able to recycle it to the fluorination reactor.

BACKGROUND OF THE INVENTION

Various techniques for carrying out the separation of HF and chlorofluorinated hydrocarbons have already been described. There may be mentioned, for example:
- U.S. Pat. No. 2,640,086, which relates to the separation of HF and chlorodifluoromethane and uses chloroform to promote the separation into two phases, a phase which is rich in HF and a phase which is poor in HF;
- U.S. Pat. No. 3,873,629, which relates to a continuous process for the separation of HF and chlorodifluoromethane and which consists in bringing the gaseous mixture of the two constituents into countercurrent contact with sulphuric acid;
- U.S. Pat. No. 3,976,447, which proposes separation of HF from gaseous effluents by absorption/desorption on particles of calcium, barium or strontium chloride;
- U.S. Pat. No. 4,209,470, which describes a process for the separation of HF from its mixtures with 1-chloro-1,1-difluoroethane to which, to improve the separation, is added a secondary liquid consisting entirely or largely of 1,1-dichloro-1-fluoroethane;
- U.S. patent application No. 0,353,970, which relates to the separation of HF from its mixtures with 2,2-dichloro-1,1,1-trifluoroethane and/or 2-chloro-1,1,1,2-tetrafluoroethane by settling and distillation.

In the case of mixtures of HF and F133a, a simple distillation does not make it possible to separate them because HF and F133a form an azeotrope which is more volatile than HF or F133a; the HF content of this azeotrope is approximately 60 molar % (20% by weight). At room temperature and whatever the concentrations of HF and F133a, the mixtures of HF and F133a do not separate into two phases.

On the other hand, it is possible to obtain an excellent separation of a mixture of HF and F133a provided that it is cooled to a temperature below 0° C., preferably of between −40° C. and −10° C. It has also been found that it is possible to further improve this separation if the settling of HF and F133a is carried out in the presence of trichloroethylene (TCE).

The presence of TCE in the mixture of F133a and HF substantially reduces the solubilities of HF in the organic phase and of the organics in the HF phase; the separation of F133a and HF is thus carried out more efficiently.

DESCRIPTION OF THE INVENTION

The subject of the invention is thus a process for the separation of HF and F133a, characterized in that it comprises a stage in which the HF/F133a mixture is subjected to a settling in the presence of TCE at a temperature below 0° C. in order to obtain an upper phase which is rich in HF and a lower organic phase which is poor in HF.

The proportion of TCE in the mixture which is subjected to settling can range from 0.05 to 2.5 mol of TCE per mole of F133a. It is preferably greater than 0.25 mol of TCE per mole of F133a and advantageously between 0.8 and 1.2 mol per mole of F133a. The TCE can optionally already be present in the initial mixture of F133a and HF (for example, in the case where the mixture to be treated would arise from a manufacture of F133a from trichloroethylene and HF) or can be added to the HF/F133a mixture (gaseous or liquid) prior to the settling. The HF/F133a/TCE mixture is then brought to the temperature and pressure conditions chosen for the settling. The latter is advantageously carried out at a temperature of between −40° and −10° C., preferably between −25° and −15° C. The pressure has no significant influence on the settling; it is thus possible to generally carry out the settling at a pressure which can range from 1 to 30 bars absolute, even if in practice it is preferable to work at a pressure ranging from 1 to 15 bars absolute.

The settling operation can be carried out continuously or noncontinuously and according to various known techniques. It can be advantageously combined with other separation operations such as distillations depending on the desired separation objective. Thus, if it is desired to obtain virtually pure F133a, virtually pure HF and virtually pure TCE for recycling, the settling can be combined with the following operations:

a) The lower organic phase which is poor in HF, obtained by settling, is distilled so as to recover HF at the head of a distillation column, in the form of an HF/F133a azeotrope which is recycled to the settler, and to recover TCE and F133a at the foot of the column.

b) The upper phase which is rich in HF, obtained by settling, is subjected to a distillation so as to recover, at the head of a distillation column, F133a in the form of an HF/F133a azeotrope which is recycled to the settler and to recover practically pure HF at the foot of the column.

c) The mixture of TCE and F133a obtained at the foot of the column mentioned in a) is subjected to a distillation so as to recover purified F133a at the head and TCE at the foot, which can, for example, be recycled to the settling.

BRIEF DESCRIPTION OF THE DRAWINGS

The invention will be described with reference to the following non-limiting drawings.

Figure 1:
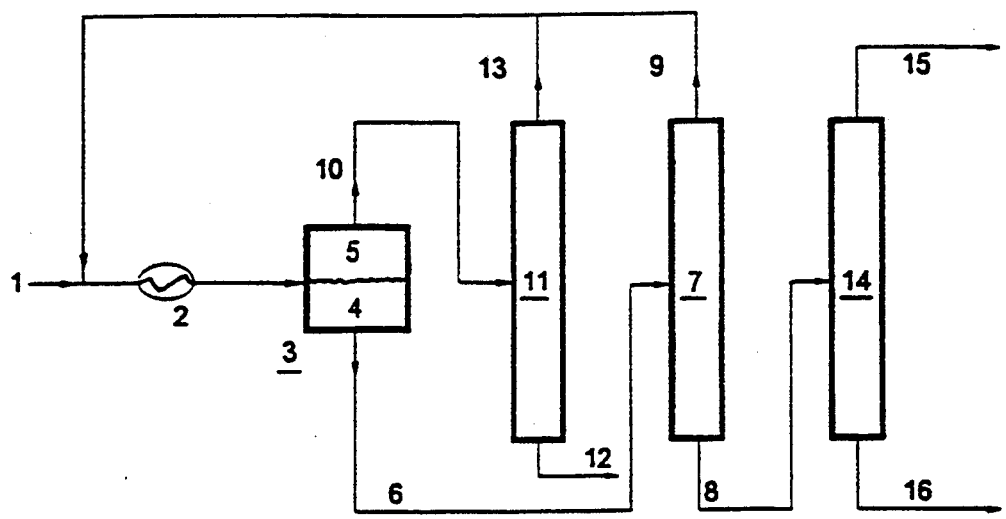
FIG. 1 shows a schematic diagram of the present process.

The operation of the process according to the invention in its complete version will be better understood by referring to the scheme of the appended FIG. 1. After optional addition of TCE, the mixture to be treated is introduced via pipe 1 in order to be cooled beforehand via the exchanger 2. It is then brought to the settler 3, maintained at a temperature below 0° C. and preferably of between −40° C. and −10° C. By demixing, there is then obtained, in the settler, a lower organic phase 4, which is poor in HF, and an upper phase 5, which is rich in HF. The organic phase 4, emerging from the settler 3, supplies, via 6, a distillation column 7, from the top of which emerges an effluent 9 with an azeotropic composition of HF and F133a; this effluent 9 is returned to the settler 3 upstream of the exchanger 2 in order to be separated into two phases. At the foot of column 7, a flow 8 is recovered which consists of a mixture of F133a and TCE.

The flow 8 is subjected to a distillation in column 14 which makes it possible to obtain at the head, via line 15, pure F133a and at the foot, via line 16, TCE which is either used as it is or recycled upstream of the cooler 2 as flow 9.

The upper phase 5, which is rich in HF, is brought, via pipe 10, to a distillation column 11, at the head of which emerges an effluent 13, with an azeotropic composition of HF and F133a which, as effluent 9, is returned to the settler 3 upstream of the exchanger 2, in order to be separated into two phases. At the foot of column 11, practically pure HF is then recovered at 12.

Passage from the settler to the distillation columns and from the latter towards the settler is carried out via pressure-reducing valves or pumps, depending on the operating pressures of the settler and the distillation columns. The temperature of the flows which supply, via 6 and 10, the distillation columns can be adjusted using exchangers in order to obtain an optimum distillation.

Figure 2:
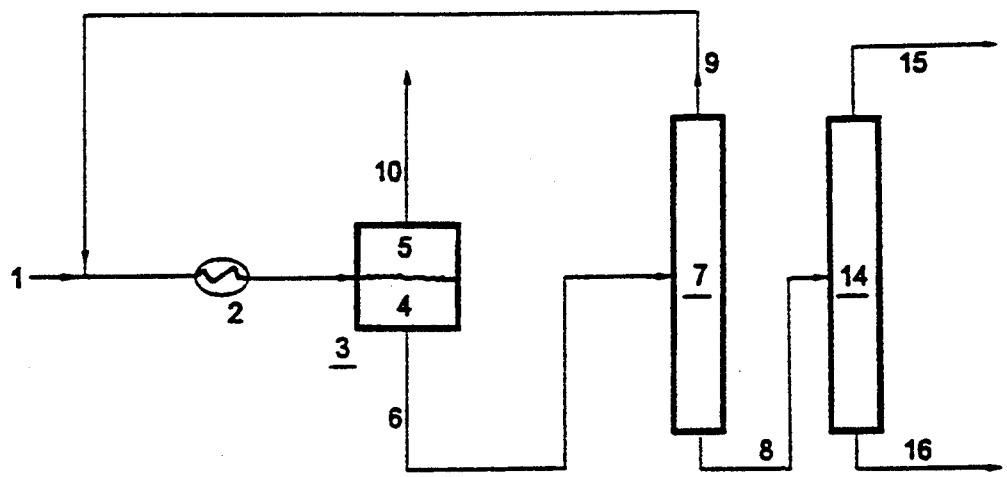
FIG. 2 shows a schematic diagram of another embodiment of the present process.

FIG. 2 illustrates another embodiment of the process where the upper phase 5, which is rich in HF, emerging via pipe 10, can be recycled as such directly to the fluorination reactor for the production of F133a.

The process according to the invention is suitable for treating mixtures containing a preponderant quantity of HF and F133a (% HF+% F133a>50 weight %, preferably>80%), it being possible for these two compounds to be present in any relative proportion. The mixtures to be treated can also contain up to 20% by weight of other fluorinated organic compounds such as, for example, difluorodichloroethane (F132b).

If the starting mixture of HF and F133a deviates substantially from the azeotropic composition, it can be advantageous to carry out beforehand a distillation in order to separate the HF/F133a azeotrope at the head from the excess compound (HF or F133a) which will remain at the foot. After condensation, the azeotropic composition is then subjected to cold settling according to the invention.

EXAMPLES

The following examples illustrate the invention without limiting it.

EXAMPLES 1 to 3

These examples show the essential advantage of carrying out the separation of F133a and HF by settling in the presence of TCE (Examples 1 and 2).

Table I gives the starting composition of the F133a, HF and TCE mixtures and the composition of the HF and organic phases obtained by settling at −20° C.

TABLE I

|  |  | EXAMPLE 1 | EXAMPLE 2 | EXAMPLE 3 (comparative) |
|---|---|---|---|---|
| Composition before settling (number of moles) | HF | 4.4 | 0.95 | 1.75 |
|  | F133a | 0.4 | 0.68 | 1.25 |
|  | TCE | 0.3 | 0.72 | — |
| Composition after settling (weight %) | Organic phase: |  |  |  |
|  | HF | 0.57 | 1.6 | 4.25 |
|  | F133a | 41.75 | 44.5 | 95.75 |
|  | TCE | 57.68 | 53.9 | — |
|  | Inorganic phase: |  |  |  |
|  | HF | 82.71 | 80.5 | 61.14 |
|  | F133a | 16.00 | 18.5 | 38.86 |
|  | TCE | 1.29 | 1.0 | — |

Examination of Table I makes it possible to confirm the marked reduction in the solubilities of the HF in the organic phase and of the organics in the HF phase when TCE is present.

EXAMPLE 4

This example illustrates the complete implementation of the process for producing virtually pure HF, F133a and TCE, according to FIG. 1.

The initial mixture of F133a and HF has the following composition: HF 58 mol % and F133a 42 mol %. TCE is added to this mixture to obtain the following composition: HF 40 mol %, F133a 29 mol % and TCE mol %.

Table II gives the composition and the pressure and temperature conditions of various flows with reference to FIG. 1.

TABLE II

|  | Organic phase (4) | HF phase (5) | Head of columns 7 and 11 (9 and 13) | Foot of column 7 (8) | Foot of column 11 (12) | Head of column 14 (15) | Foot of column 14 (16) |
|---|---|---|---|---|---|---|---|
| HF (mol %) | 8.5 | 96.0 | 60 | — | 100 | — | — |
| F133a (mol %) | 41.4 | 3.8 | 40 | 50 | — | 100 | — |
| TCE (mol %) | 50.3 | 0.2 | — | 50 | — | — | 100 |
| Temperature (°C.) | −20 | −20 | 66 | 108 | 96 | 17 | 100 |
| Pressure (bars absolute) | 15 | 15 | 10 | 10 | 10 | 1.5 | 1.5 |

We claim:
1. Process for the separation of hydrogen fluoride (HF) from its mixtures with 1,1,1-trifluoro-2-chloroethane (F133a), comprising a stage in which the HF/F133a mixture to be treated is subjected to a set- tling in the presence of trichloroethylene (TCE) at a temperature below 0° C. in order to produce an upper phase which is rich in HF and a lower organic phase which is poor in HF.

2. Process according to claim 1, wherein the mixture subjected to settling contains from 0.05 to 2.5 mol of TCE per mole of F133a.

3. Process according to claim 1, in which the mixture subjected to settling contains from 0.8 to 1.2 mol of TCE per mole of F133a.

4. Process according to claim 1, wherein the settling temperature is between −40° and −10° C.

5. Process according to claim 1, wherein, before the settling operation, the HF/F133a mixture is optionally subjected to a distillation in order to bring it to a composition in the region of an azeotropic composition.

6. Process according to claim 1, wherein, after settling:
   a) the lower organic phase, which is poor in HF, obtained is distilled so as to separate, at the head, the HF contained in this phase, in the form of an HF/F133a azeotrope which is returned to the settler, and to recover, at the foot, a mixture of F133a and TCE, and
   b) the upper phase, which is rich in HF, is either recycled directly to the fluorination reactor or subjected to a distillation so as to separate, at the head, the F133a azeotrope which is returned to the settler, and to recover, at the foot, practically pure HF.

7. Process according to claim 6, wherein the mixture of F133a and TCE is subjected to a distillation so as to separate, at the head, pure F133a and to recover, at the foot, pure TCE.

8. Process according to claim 1, wherein the mixture of HF and F133a to be treated additionally contains up to 20% by weight of other fluorinated organic compounds.

9. Process according to claim 2, wherein the mixture contains more than 0.25 mol of TCE per mole of F133a.

10. Process according to claim 4, wherein the settling temperature is between −25° and −15° C.

* * * * *